United States Patent

Palsson

[11] Patent Number: 6,143,535
[45] Date of Patent: *Nov. 7, 2000

[54] TARGETED SYSTEM FOR REMOVING TUMOR CELLS FROM CELL POPULATIONS

[76] Inventor: Bernhard O. Palsson, 730 Fern Glen, La Jolla, Calif. 92037

[*] Notice: This patent is subject to a terminal disclaimer.

[21] Appl. No.: 09/049,677

[22] Filed: Mar. 27, 1998

Related U.S. Application Data

[63] Continuation-in-part of application No. 08/824,968, Mar. 27, 1997, Pat. No. 5,874,266.

[51] Int. Cl.[7] .............................. C12N 13/00; A61K 35/18

[52] U.S. Cl. .................................... 435/173.1; 435/173.4; 435/173.7; 424/577

[58] Field of Search .............................. 435/173.1, 173.4, 435/173.7; 424/577

[56] References Cited

U.S. PATENT DOCUMENTS

| | | | |
|---|---|---|---|
| 4,284,897 | 8/1981 | Sawamura et al. | 250/461.2 |
| 4,395,397 | 7/1983 | Shapiro | 424/577 |
| 4,532,402 | 7/1985 | Overbeck | 219/121.78 |
| 4,624,915 | 11/1986 | Schindler et al. | 435/4 |
| 4,629,687 | 12/1986 | Schindler et al. | 435/4 |
| 4,803,992 | 2/1989 | Lemelson | 600/342 |
| 5,035,693 | 7/1991 | Kratzer et al. | 606/12 |
| 5,089,384 | 2/1992 | Hale | 435/173.4 |
| 5,158,889 | 10/1992 | Hirako et al. | 435/286.3 |
| 5,188,633 | 2/1993 | Kratzer et al. | 606/12 |
| 5,272,081 | 12/1993 | Weinreb et al. | 435/29 |
| 5,298,963 | 3/1994 | Murakami et al. | 359/389 |
| 5,381,224 | 1/1995 | Dixon et al. | 356/72 |
| 5,646,411 | 7/1997 | Kain et al. | 250/458.1 |
| 5,672,880 | 9/1997 | Kain | 250/458.1 |
| 5,690,846 | 11/1997 | Okada et al. | 219/121.78 |
| 5,719,391 | 2/1998 | Kain | 250/235 |
| 5,874,266 | 2/1999 | Palsson | 435/173.1 |
| 5,932,872 | 8/1999 | Price | 250/201.3 |

OTHER PUBLICATIONS

Photonic Instruments, Inc.; Micro Point–Laser System For Bio–Medical and Life Sciences; Product Information Sheet, Apr., 1996.

Gribben, et al.; Antibody–mediated Purging; *Bone Marrow Transplantation*; Chapter 13, Boston–Blackwell Scientific Publications; pp. 149–163 (1994).

Rowley, Scott D.; Pharmacological Purging of Malignant Cells; *Bone Marrow Transplantation*; Chapter 14, Boston–Blackwell Scientific Publications; pp. 164–178 (1994).

Gee, Adrian P.; Part 5: Autologous Bone Marrow Purging; *Bone Marrow Processing and Purging*; pp. 248–328 (1991), CRC Press, Boca Raton.

Dooley, et al.; A Novel, Inexpensive Technique for the Removal of Breast Cancer Cells from Mobilized Peripheral Blood Stem Cell Products; *Blood*; vol. 88, p. 252a (1996), Abst. 995.

Greer, et al.; A Clonogenic Culture Method for the Identification of Breast Cancer Cells in Marrow Aspirates of Patients Receiving High–Dose Chemotherapy; Abstract 996, *Blood* (1996), vol. 88, p. 252a.

Thomas, et al.; Direct Purging of Breast Carcinoma Cells with Anti–CD24 and/or Anti–Breast Carcinoma Antibodies Using a Novel Immunomagnetic Cell Depletion System; *Blood* (1996), vol. 88, p. 252a, Abst 997.

Theocharous, et al.; The Detection and Genetic Analysis of Low Frequency Epithelial Tumour Cells in Patients with Breast Cancer; *Blood* (1996), vol. 88, p. 252a, Abstr 997.

(List continued on next page.)

*Primary Examiner*—Jon P. Weber
*Attorney, Agent, or Firm*—Knobbe, Martens, Olson & Bear, LLP

[57] ABSTRACT

A method is presented to remove contaminating tumor cells from a cell population. The method includes labeling individual tumor cells in the population and then killing them with a high energy laser beam. The laser is focused so that it specifically kills the identified tumor cell, but not the remaining cells in the population.

32 Claims, 2 Drawing Sheets

OTHER PUBLICATIONS

Miller, et al.; Rapid Killing of Single Neurons by Irradiation of Intracellularly Injected Dye; *Science*; vol. 206; Nov. 9, 1979; pp. 702–704.

Lazarus, et al.; Does In Vitro Bone Marrow Purging Improve the Outcome after Autologous Bone Marrow Transplantation?; *Journal of Hematotherapy*; 1993; 2:457–466.

Gulati, et al.; Rationale for Purging in Autologous Stem Cell Transplantation; *Journal of Hematotherapy*; 1993; 2:467–471.

Brugger, et al.; Mobilization of Tumor Cells and Hematopoietic Progenitor Cells Into Peripheral Blood of Patients with Solid Tumors; *Blood*; vol. 83; No. 3; Feb. 1, 1994; pp. 636–640.

Rill, et al.; Direct Demonstration that Autologous Bone Marrow Transplantation for Solid Tumors Can Return a Multiplicity of Tumorigenic Cells; *Blood*; vol. 84; No. 2; Jul. 15, 1994; pp. 380–383.

Campana, et al.; Detection of Minimal Residual Disease in Acute Leukemia: Methodologic Advances and Clinical Significance; *Blood*; vol. 85; No. 6; Mar. 15, 1995; pp. 1416–1434.

Gazitt, et al.; Purified CD34+Lin–Thy+Stem Cells Do Not Contain Clonal Myeloma Cells; *Blood*; vol. 86; No. 1; Jul. 1, 1995; pp. 381–389.

Clarke, et al.; A recombinant bcl–xs adenovirus selectively induces apoptosis in cancer cells but not in normal bone marrow cells; *Proc. Natl. Acad. Sci. USA*; vol. 92; Nov. 1995; pp. 11024–11028.

Lydaki, et al.; Merocyanine 540 mediated photoirradiation of leukemic cells. In vitro inference on cell survival; *Journal of Photochemistry and Photobiology B: Biology 32*; pp. 27–32, 1996.

TARGETED SYSTEM FOR REMOVING TUMOR CELLS FROM CELL POPULATIONS

RELATED APPLICATION

This application is a continuation-in-part of U.S. application Ser. No. 08/824,968, filed on Mar. 27, 1997, now U.S. Pat. No. 5,874,266.

BACKGROUND OF THE INVENTION

1. Field of the Invention

This invention relates to methods and apparatus for specifically isolating tumor cells from a population of non-tumor cells, In particular, this invention relates to methods and apparatus for specifically labeling and thereafter individually killing tumor cells with a focused high-energy beam such as a laser beam.

2. Description of the Related Art

Hematopoietic stem cell transplantation is a rapidly growing therapy throughout the world. Hematopoietic stem cells are cells that reside in the bone marrow and lead to the production of all of the body's blood cells. In 1995, over twenty thousand hematopoietic stem cell transplants were performed in the United States. In particular, the treatment of breast cancer with autologous hematopoietic stem cell transplantation has become a widely used cancer therapy.

Tumor metastasis is a well-known process by which tumor cells leave their initial location and spread to other parts of the body. Once transported to a new site, the tumor cells begin to grow and populate the new site, thus creating a new tumor. One treatment for patients with metastatic tumors involves harvesting their hematopoietic stem cells and then treating the patient with high doses of radiotherapy or chemotherapy. This treatment is designed to destroy all the patients tumor cells, but has the side effect of also destroying their hematopoietic cells. Thus, once the patient has been treated, the autologous stem cells are returned to their body.

However, if the tumor cells have metastasized away from the tumor's primary site, there is a high probability that some tumor cells will contaminate the harvested hematopoietic cell population. In such a case, the harvested hematopoietic stem cells include contaminating tumor cells. It is important to find a mechanism for killing all of the metastasized tumor cells prior to reintroducing the stem cells to the patient. If any living tumorigenic cells are re-introduced into the patient, they can lead to a relapse.

The problem of removing tumor cells from hematopoietic cells has been reported during traditional bone marrow harvest procedures (Campana, D. et al. *Detection of minimal residual disease in acute leukemia: methodologic advances and clinical significance*, Blood, Mar. 15, 1995 85(6): 1416–34). Similar problems were also found when others attempted to remove tumor cells with the newer method of leukopheresis of mobilized peripheral blood cells (Brugger, W. et al. *Mobilization of tumor cells and hematopoietic progenitor cells into peripheral blood of patients with solid tumors* Blood, 83(3): 636–40, 1994).

In each of these procedures, the number of contaminating tumor cells ranged from about 10 to 5000 tumor cells per four million mononuclear harvested cells, depending on the chemotherapeutic drug regimen used for mobilization. Mononuclear cells were obtained by a discontinuous density gradient centrifugation of the entire hematopoietic cell harvest. The total number of mononuclear cells harvested from a patient is normally on the order of 10 billion cells. Thus, the total tumor burden in a harvest varies from a lower boundary of about 25 thousand cells to a higher boundary of about 12 million cells.

These contaminating tumor cells have been shown by genetic marking to contribute to tumor relapse (Rill, ER et al., *Direct Demonstration That Autologous Bone Marrow Transplantation for Solid Tumors Can Return a Multiplicity of Tumorigenic Cells*, Blood, 84(2): 380–383, 1994). Thus, a great need exists for efficient methods for removing all of the tumor cells from a hematopoietic cell transplant (Gulati, SC et al *Rationale for purging in autologous stem cell transplantation*. *Journal of Hematotherapy*, 2(4):467–71, 1993). A rapid and reliable method for removing all of the contaminating tumor cells would improve the efficacy of hematopoietic stem cell transplantation for a growing number of patients.

Others have attempted to remove contaminating tumor cells from hematopoietic stem cell harvests, but have met with limited success. Several methods of purging the tumor cell populations away from the harvested stem cells have been proposed and tested (A. Gee, Editor Bone Marrow Processing and Purging, Part 5, CRC Press, Boca Raton, Fla., 1991). Thus, the idea underlying all of these purging methods is to separate or destroy the malignant cells while preserving the hematopoietic stem cells that are needed for hematopoietic reconstitution in the transplantation patient.

Some companies and physicians have attempted to purge malignant cells away from populations of non-tumor cells using an immunoaffinity bead-based selection. In this procedure, the total cell population is contacted by immunoaffinity beads. For example, to isolate tumor cells from hematopoietic cells, a first (positive) CD34 selection isolates hematopoietic cells from tumor cells. Binding hematopoietic-cell-specific anti-CD34 antibodies to the immunoaffinity beads allows the physician to specifically remove these cells from populations of non-hematopoietic cells. In some instances, a negative immunoaffinity bead-based selection is also run on tumor or epithelial cell markers by conjugating tumor-specific antibodies to the beads.

Another method that has been tried for removing tumor cells from populations of non-tumor cells involved immunoconjugating a toxic agent to an antibody having specificity for only the tumor cells. In this system, antibodies were bound to chemotoxic agents, toxins, or radionucleides and then contacted with the harvested cell population. Unfortunately, not all of the tumor cells were killed by this treatment.

Other systems for isolating tumor cells from non-tumor cell populations have used the non-specific binding characteristics of hematopoietic cells as the basis for separation. For example, Dooley et al. used these adhesive characteristics to isolate hematopoietic cells with deep bed filtration (Dooley DC et al., *A novel inexpensive technique for the removal of breast cancer cells from mobilized peripheral blood stem cell products*, Blood, 88(10)suppl 1: 252a, 1916). However, some of the tumor cells were found to isolate with the hematopoietic cells, thus opening the door for a potential relapse by the patient.

In addition, cytotoxic agents, such as 4-Hydroxy-peroxy-cyclo-phosphamide (4HC), have been used to selectively kill tumor cells without damaging the hematopoietic stem cells. Unfortunately, this system also led to lower harvests of hematopoietic cells because the cytotoxic agents weakened or destroyed some of the non-tumor cells.

In other methods, sensitizing agents, such as merocynanine, were mixed with the cell populations which were thereafter photo-irradiated to specifically kill the tumor cells (Lydaki et al. *Merocyanine 540 mediated photoirradiation of leukemic cells Journal of Photochemistry and Photobiology* 32(1–2):27–32., 1996). Also, Gazitt et al. used fluorescence activated cell sorting (FACS) to sort hematopoietic stem cells from tumor cells (Gazitt et al. *Purified CD34+Lin–Thy+stem cells do not contain clonal myeloma cells Blood,* 86(1):381–389, 1995). As is known, flow cytometry sorts cells one at a time and physically separates one set of labeled cells from another second set of cells. However, it has been shown that individual neurons can be killed after loading them with the adsorbing dyes used in flow cytometry (Miller, JP and Selverston AI., *Rapid Killing of Single Neurons by irradiation of Intracellularly injected dye Science,* 206:702–704, 1979). Thus, using FACS to separate cell populations is not advantageous because the cell yields can be very low.

In another protocol, Clarke et al. disclosed the use of adenovirus mediated transfer of suicide genes to selectively kill tumor cells (Clarke et al. *A recombinant bcl-x s adenovirus selectively induces apoptosis in cancer cells but not in normal bone marrow cells Proc. Nat. Acad. Sci.* 92(24):11024–8, 1995).

However, most of the methods listed above are based on administering a whole-population based tumor cell separation or killing strategy. Unfortunately, the whole population tumor purging methods listed above do not kill or remove all of the contaminating tumor cells from the harvested stem cell population. In the best case, the residual tumor cell burden remained at 1 to 10 tumor cells for every 100,000 cells present in the initial harvest (Lazarus et al. *Does in vitro bone marrow purging improve the outcome after autologous bone marrow transplantation? Journal of Hematotherapy,* 2(4):457–66, 1993).

Therefore, even using the best available techniques, the number of residual tumor cells that are reintroduced into the patient during autologous stem cell transplantation is on the order of 10 to 2000 cells. Given the rapid exponential growth of tumor cells, such residual tumor cells in the transplant can quickly lead to a patient's relapse.

A still further method utilizing laser technology is described in U.S. Pat. No. 4,395,397 to Shapiro. In the Shapiro method, labeled cells are placed in a flow cytometer having a fluorescence detector to identify the labeled tumor cells. A laser beam is used to kill the labeled cells as they pass by the detector. This method suffers from a number of disadvantages. Firstly, once an unwanted cell has passed through the detector/laser region there is no way to check that destruction has been completed successfully. If a tumor cell evades destruction it will inevitably be reintroduced into the patient. Secondly, the focal spot diameter of the laser beam is of necessity greater than the liquid stream cross section. Accordingly, many of the cells in the region of an unwanted cell will be destroyed by the laser beam, including healthy cells.

Another method that utilizes laser technology is described in U.S. Pat. No. 5,035,693 to Kratzer. In this method, labeled cell populations are placed on a moving belt. The labeled cells are thereafter identified by a detector and destroyed by a laser. However, this system has many of the same disadvantages as the Shapiro method. For example, because the cells are moving on a belt past the detector in one direction, the method is not reversible. Thus, if a single tumor cell escapes detection, it will be reintroduced into the patient.

Thus, in spite of extensive efforts and many innovative approaches, there exists a great and growing need for methods and systems for eradicating virtually every tumor cell from a harvested cell population. The system and method described herein fulfills this need.

SUMMARY OF THE INVENTION

This invention provides a targeted system and method of individually identifying and destroying contaminating tumor cells in a cell population. Using the system of the present invention, virtually every tumor cell can be identified and individually destroyed. Thus, autologous hematopoietic cell transplantation and similar medical techniques can be performed without re-introducing any contaminating tumor cells.

Tumor cells can be identified with the disclosed invention using several approaches. One embodiment includes a non-destructive labeling method so that all of the viable tumor cells are distinguishable under a microscope from the non-tumor cells. In this embodiment, a tumor-specific fluorochrome-conjugated antibody can be used to specifically mark each of the tumor cells, yet not mark any of the hematopoietic cells. The labeled tumor cells are then microscopically identified within the population of non-tumor cells. A narrow, high power laser beam is thereafter focused on each of the identified tumor cells and a brief, lethal light pulse is delivered. The next tumor cell is then identified and killed, and so on until every marked tumor cell is destroyed.

In another embodiment, an antibody that selectively binds to hematopoietic cells, but not tumor cells, is used to identify hematopoietic stem cells. All of the tumor cells (eg: those that do not take up label) are identified and thereafter killed with a narrow, high power laser beam.

Yet another embodiment is a method of eliminating tumor cells from within a population of cells that includes non-tumor cells, including the steps of: a) labeling the population of cells so that the tumor cells can be distinguished from the non-tumor cells; b) locating one of the tumor cells by reference to the label; and c) killing the tumor cell by applying a pulse from a controlled energy source to the located tumor cell.

One additional embodiment is a method for enriching the number of stem cells in a hematopoietic cell population, including: a) labeling the hematopoietic cell population with a stem cell specific label; and b) applying a high-energy laser-light pulse to at least one of the un-labeled cells in the population.

Still another embodiment is a method for preparing isolated hematopoietic cells for re-introduction into a patient, including: a) labeling tumor cells within the isolated hematopoietic cells with a tumor cell specific label; and b) applying a high-energy laser-light pulse to at least one of the labeled cells in the population.

Another embodiment of the invention is an in vitro method for ensuring that a first population of cells has been eliminated from a second population of cells, comprising. The method includes: labeling the first population of cells so that the first population of cells can be distinguished from the second population of cells; placing the first population of cells and the second population of cells is in a stationary position on a surface; locating one cell in the first population of cells by reference to the label; applying a first pulse from a controlled energy source to the one cell; determining if the one cell was killed by the first pulse; and applying a second pulse from a controlled energy source if the one cell was not killed.

A further embodiment of the invention is a method of eliminating tumor cells from within a cell population that includes non-tumor cells. The method includes the steps of: labeling the non-tumor cells so that the non-tumor cells can be distinguished from the tumor cells, locating one of the tumor cells by identifying a non-labeled cell in the cell population; and killing the tumor cell by applying a pulse from a controlled energy source to the located tumor cell while the tumor cell is in a substantially stationary position on a surface.

DETAILED DESCRIPTION

Figure 1:
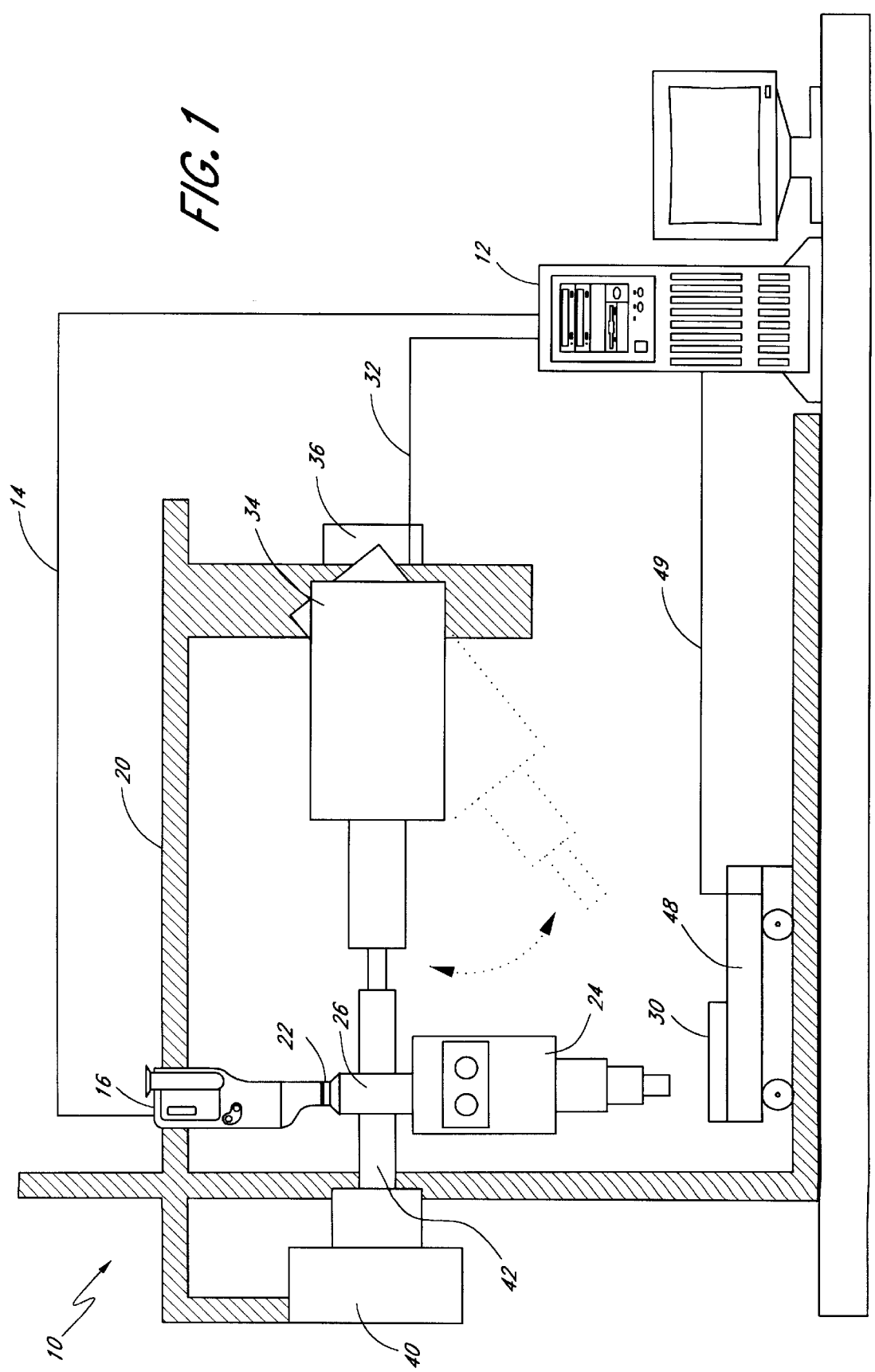
FIG. 1 is a diagram of one embodiment of an automated system for specifically targeting labeled cells. The system includes a computer, a camera, a broad-band light source and a laser.

A targeted method is provided for removing contaminating tumor cells from a population of non-tumor cells. As discussed above, this method relates to medical procedures whereby populations of cells are removed and then re-introduced into patients as part of a therapeutic regime. Generally, the targeted method first employs a label that acts as a marker to microscopically identify and locate the contaminating tumor cells.

The chosen cellular marker can be any label that identifies and discriminates a contaminating tumor cell residing within a population of non-tumor cells. For example, anti-tumor antibodies that are conjugated to a fluorochrome can be used as specific labels (See Chapter 10 in A. Gee, Editor, *Bone Marrow Processing and Purging*, Part 5, CRC Press, Boca Raton, Fla., 1991). Numerous tumor-specific makers have been found on a wide variety of tumorigenic cells, For example, many surface markers that are specific to epithelial cells have been found on contaminating breast cancer cells in harvested hematopoietic cell populations. Such antibodies can be used to identify breast cancer cells within hematopoietic cell populations and therefore target them for the delivery of a lethal energy pulse. Similarly, other tumor-specific fluorochrome-conjugated antibodies can be used to identify other types of contaminating tumor cells.

It should also be noted that if no specific markers are available for the tumor cell population, the method can be implemented in an 'inverse' fashion. Specific markers for the non-tumor cell population can be used to identify those cells that are not tumorigenic. For example, in hematopoietic cell populations, the CD34 cell marker can be used to stain only the hematopoietic cells, but not the non-hematopoietic tumor cells. Any cell that does not have the marker is then killed by the delivery of a focused energy pulse. The remaining viable cell population will only contain the cells that possessed the cell marker (eg: CD34).

After the tumor cells are identified, a controlled energy source, such as a laser, collimated or focused non-laser light, RF energy, accelerated particle, focused ultrasonic energy, electron beam, or other radiation beam is used to deliver a targeted lethal energy pulse that individually kills each of the tumor cells. Because the tumor cells can be specifically and uniquely identified within a population of non-tumor cells, the method can be used to completely eradicate just the contaminating tumor cells.

In one embodiment of the targeted method, the tumor cells are killed by simultaneous fluorescence and laser illumination. In a first step, the cell population is stained with a fluorescent stain that is specific for tumor cells. For example, antibodies that are specific for tumor cells and conjugated to fluorescent molecules could be used in this embodiment. The cell population is then illuminated by an appropriate light (e.g., ultraviolet light) so that the fluorescent tumor cells can be identified within the population of non-tumor cells.

The labeled cells are then placed in a Petri dish and placed within the system. If the system is in an automatic mode, a fluorescent light is illuminated and a CCD camera begins taking video pictures of the cells in the dish. A computer program running on an attached computer begins analyzing the pictures and identifying every one of the fluorescent cells. Each cell is targeted and destroyed with a laser beam. The computer confirms that each cell is killed by noting the change in fluorescence before and after the laser has been activated.

In another embodiment, contaminating cells in biopsies are removed from cancer patients. The in vitro establishment of primary human tumor cell lines from many tumor types is complicated by the presence of contaminating primary cell populations that have superior in vitro growth characteristics over tumor cells. For example, contaminating fibroblasts represent a major challenge in establishing many cancer cell lines. The disclosed system could be used to particularly label and destroy the contaminating cells, while leaving the biopsied tumor cells intact. Accordingly, the more aggressive primary cells will not overtake and destroy the cancer cell line.

In a related application, the present system could be used to remove contaminating cells in inocula for tissue engineering and cell therapy applications. Cell contamination problems exist in the establishment of primary cell cultures for tissue engineering applications and in the implementation of cellular therapies. In particular, chondrocyte therapies for cartilage defects are hampered by impurities in the cell populations derived from cartilage biopsies. Accordingly, the present system could be used to specifically remove these types of cells from the inocula. For example, a cartilage biopsy can be taken and the sample grown under conventional conditions. The growing culture is then stained with a specific label for the contaminating cells. The entire cell population is then placed within the system described below and the labeled, contaminating cells are destroyed.

In another embodiment, the significant risk and severity of Graft Versus Host Disease (GVHD) in the allogeneic Human Stem Cell (HSC) transplant setting can be combated. By using the system described herein, it is possible to define and control a patient's T cell content. This type of control is particularly difficult with existing technology, because over-depletion of T cells results in loss of the known beneficial graft versus leukemia effect that is observed in allogeneic transplants. Thus, some level of T cells is beneficial to the patient in order to attack, for example, leukemia cells. However, too high of a T-cell level leads to general immune system attacks on the recipient's tissues. The present system and methods are capable of precisely controlling the number of T cells in any allogeneic transplant.

One embodiment of an automated targeting system 10 is illustrated in FIG. 1. A computer system 12 communicates through a cable 14 to a camera 16. The computer system can be any commercially available computer that can receive and analyze video data. One example of such a computer system is an Intel Pentium Pro computer running Microsoft Windows 95 software.

Although a video camera is illustrated in the embodiment disclosed in FIG. 1, the camera 16 can be any type of image gathering equipment known to those in the art. The camera 16 is mounted onto a support 20 so that it is held in a generally vertical orientation with respect to the ground.

The lens 22 of the camera 16 is designed to mate with a microscope 249 through an eyepiece 26. Thus any image that is transmitted into the microscope 24 is sent through the eyepiece 26 to the lens 22 of the camera 16.

The camera 16 transmits the images that it captures to the computer 12 through the cable 14. In this manner, the computer 12 captures and analyzes any images that are presented to the microscope. For example, the microscope 24 may be focused on cells in a dish 30. The images of the cells will be transmitted from the microscope 24 to the camera 16, and finally be sent to the computer 12. The computer 12 can then run software to analyze the images that are captured.

The computer 12 is also in communication though a second cable 32 to a laser 34. The laser is mounted to an electronically controlled swivel 36 so that its position relative to the support 20 can be altered by receiving signals from the computer 12. As shown, the laser 34 can be adjusted to aim a light beam through the microscope 24 optics while the target cell is substantially stationary. In addition, the laser 34 can be swiveled to sent a light beam directly to the dish 30.

In the context of the present invention the term "dish" has a broad meaning. It is intended to encompass any surface capable of retaining a thin layer of fluid such as cellular medium. The dish may incorporate or be associated with cooling apparatus to keep the fluid in the dish below ambient temperature during operation of the methods described herein. It may also be desirable, but not essential, to blanket the surface of the fluid with an inert atmosphere such as nitrogen or argon.

Although the embodiment illustrated in FIG. 1 includes an electronically controlled swivel 36 to aim the laser, other methods are anticipated. For example, an electronically controlled mirror could be placed between the laser and its target so that rotation of the mirror is used to aim the laser. Other mechanisms for aiming a laser, such as beam splitters, mirrors or prisms that are known in the art are meant to be included within the scope of the invention.

A broad-band light source 40 is also in communication with the microscope 24 through an adapter 42. The adapter 42 allows light emissions from the broad-band light source to illuminate cells that are placed on the dish 30. Broad-band light sources are well known in the art, and many different types could be placed within the automated targeting system 10 to illuminate labeled cells that are placed on the dish 30.

Below and supporting the dish 30 is a computer-controlled, movable tray 48. The computer 12 can send signals along a communication cable 49 that cause the tray 48 to change its position relative to the laser 34 and microscope 24. Thus, to specifically target cells, the computer 12 can send signals along the cable 49 to the tray 48 that cause the dish 30 to be rolled into a particular position. By calculating the correct position, the laser can be aimed towards a particular cell by moving the dish 30 into a chosen position. The coordinates of the chosen position can be determined by the computer 12 from analyzing cellular images that are gathered from the camera 16.

Software that is running on the computer 12 captures the images that are transmitted through cable 14 from the camera 16. If a set of labeled cells are placed in the dish 30, then the camera 16 will record a picture of the labeled cells. As discussed above, the cells can be illuminated with the broad-band light source 40. By overlaying a two-dimensional grid on top of the picture gathered by the computer, the software can determine the X/Y coordinates of the cells that are labeled by looking for dark spots that are one cell width in diameter. The software then calculates the Cartesian coordinates of the labeled cells and specifically aims the laser 34 to those coordinates. By emitting a short, high-energy pulse, the laser can selectively kill each of the labeled cells and not damage any of the non-labeled cells.

The computer system 12 can also have sensors that detect fluorescent signals from stained tumor cells and then calculate the coordinate position of the first tumor cell to destroy The computer system then aims a focused energy source, such as a laser or electronic beam, at the calculated position of the first tumor cell. The targeted tumor cell is thereby specifically destroyed within the non-tumor cell population. This is facilitated by the fact that the target cell is substantially stationary during the procedure.

In another exemplary system, the cells are mounted for movement on a computer-controlled X-Y table under a microscope coupled with a CCD digital camera. The laser is mounted to the microscope such that it is aimed at a specific fixed location within the field of view. The computer then scans continuously across a first row of cells in the X direction until a stained tumor cell is visualized.

The computer then moves the X-Y table until the tumor cell is in the target area of the laser; the laser is pulsed to destroy the cell; then the X-Y table is returned to its previous position and is moved along the X direction until a first row is scanned and all tumor cells within that row are destroyed.

The X-Y table is then moved in the Y direction until a second row is visualized, overlapping the first row by a few cells. The table is then moved in the -X direction, tumor cells are destroyed as above, and the procedure is repeated until the entire cell population has been scanned. Preferably, the computer software automatically identifies and targets the cells. However, it is also contemplated that an operator-controlled pointing device (e.g., trackball, joystick, or mouse) could be used to locate and mark tumor cells on a display screen and/or to control movement of the X-Y table. Of course, many variations of the computer control system are possible, including alternative methods for scanning the cells and movement of the laser relative to the microscope (e.g., in the Y direction only, or anywhere within the field). It is also envisaged that the dish/table could remain substantially stationary and the microscope/laser combination could move to target labeled cells.

For example, the microscope head and laser targeting system can be moved while the flask or Petri dish holding the cells is stationary on a surface. Additionally the laser system can fire from either from or above the cell population. Because the laser targeting system is focussed through a microscope, the laser beam can be directed to different focal planes. Thus, cells that are located at different vertical heights can be specifically killed by targeting the laser beam to varying focal planes. For example, once the computer, through a detector, has identified a cell at a particular X and Y coordinate, the laser can be fired into several focal planes at those coordinates. This ensures that the cell, no matter where it is located in the vertical plane, will be killed by the laser.

The entire population of tumor cells can be automatically destroyed by repeating this targeted procedure for every tumor cell in the population. The procedure of labeling, identifying and killing each tumor cell can also be carried out manually, whereby each labeled tumor cell is microscopically identified by an operator and the laser beam is then focused by the operator on the illuminated tumor cells A combined laser/microscope system that allows manual targeting of cells is available from Photonic Instruments (Arlington Heights, Ill.).

For example, a Nikon7 Diaphot 300 microscope that allows visualization of successive adjacent fields can be utilized to view the entire cell population in a reasonable time. An exemplary cell population of $1.5 \times 10^8$ cells, at confluence, will occupy an area of 300 cm. Assuming a field of view of $2 \times 1.5$ mm at a magnification of 4×, the microscope would need to scan a $100 \times 100$ matrix, or 10,000 fields in total. A manual operator can scan perhaps 500–1000 fields per hour, so the total manual procedure would take approximately 10–20 hours. The automated procedure would be much faster.

Once the entire population of cells has been treated with an identification agent, such as a fluorescent-labeled antibody, and then killed by an energy pulse, the cell population is washed according to the patient's individual clinical needs. The population of treated cells is thereafter ready to be transplanted into the chosen patient. As discussed above, the patient is normally the same person as the original donor of the cell population.

A preferred focused energy source for the targeted method is a laser that transmits wavelengths of light in the range of 375 to 900 nanometers. One such laser is made by Photonic Instruments (Arlington Heights, Ill.). As is known, lasers provide a monochromatic light source with highly specific directionality, making it possible to aim a microscopically focused beam of energy having a diameters of only 0.5 microns.

High precision, both in terms of spatial and temporal resolution, in the delivery of light energy can be achieved at predefined wavelengths. The most advantageous wavelength that will kill a particular tumor cell can be determined experimentally and employed for the most advantageous results. In addition, pulse lengths of approximately 10–100 nanoseconds can be used to specifically kill only a single cell in the population.

As an alternative, broad-band light sources (e.g. as obtained from a Xenon Lamp) can be narrowly focused by employing an automated iris to provide a controlled energy source A high-powered broad-band light-source can be focused on areas as small as one square-micron and thus selectively used to kill a single tumor cell within a population of non-tumor cells.

The power of the light source, and the duration of the light pulse, can be adjusted to achieve the desired result of specifically killing a particular tumor cell. Laser pulse lengths can be as short as 2 to 6 nanoseconds, and light energy can be emitted at up to 50 microjoules or more. However, the total amount of light energy provided to the designated target cell is preferably selected not to cause substantial boiling of the targeted cellular material or the surrounding medium.

Locally heating the cellular medium to the point of boiling can cause the field of view to become clouded, thus disrupting an automated targeting system. In addition, there is a risk that non-tumor cells that are located next to the targeted cell will become damaged. In one embodiment, the total light power delivered will minimally disrupt the cellular membrane thereby leading to eventual cell death through the loss of cytoplasmic components. Alternatively, the total light power can be chosen to irreversibly damage cellular components, thus leading to cell death without destruction of the cellular membrane.

To microscopically observe the tumor cells, the total cell population can be advantageously placed in a nominally flat surface so that a large number of cells appear in a single focal plane. The density of cells on this surface can, in principle, be at any value. However, the cell density should be as high as possible to minimize the total surface area required for the procedure. If the contaminating cells are clearly identifiable, the total cell population can be placed on the surface at confluence (about 500,000 cells per square centimeter).

If the population of harvested cells are hematopoietic cells that were removed as part of a bone marrow transplant, then enriching the population for only the desired stem cells will allow the population to be observed in a smaller total area. For instance, to observe a CD34-enriched population of 350 million (5 million per kilogram in a 70 kilogram patient) hematopoietic cells, the total surface area required is approximately 700 square centimeters. However, if the hematopoietic stem cell enrichment procedures included screening for multiple stem cell specific markers, the total number of target cells would decrease, thereby requiring a smaller total area for the targeted procedure As is known, hematopoietic populations can be enriched for stem cells based on expression of the stem cell markers Thy-1, CD38, CD15, CD11b, Gly-A, CD3, or CD19. In addition, the cells can be enriched by the well-known techniques of deep bed filtration or counterflow elutriation.

If the tumor cell detection is not hampered at cell confluency, then it may be desirable to keep the target cell population at subconfluency so that collateral damage to neighboring cells is minimized. However, because the total number of cells is large compared to the number of tumor cells, some collateral damage to surrounding cells can be tolerated. Detection and location of labeled tumor cells in a three dimensional space using confocal microscopy would remove the need for a flat surface and the identification and focusing of the lethal light source can take place though a volume in which the cells are placed.

After the tumor cells have been specifically destroyed, the cellular debris can be removed by washing the cells at a low temperature. Depending on the projected length of the procedure, the target cell population can be cooled to 4° C. so that the contaminant removal process will proceed with only a minimum degradation in physiological performance of the non-tumor cell population This can be especially important when the non-tumor cells are hematopoietic cells, since they are subject to degradation at room temperature. A thermoelectric cooling device can be used during this procedure to cool the cell population.

As is known, cooling the cell population to 4° C. eliminates all cell motion. The surface on which the cells are placed can also be coated with polycationic compounds, such as poly-l-Lysine, so that the cells stick tightly.

The following example illustrates one embodiment of the targeted method for removing tumor cells from a population of hematopoietic cells.

EXAMPLE 1

Hematopoietic Stem Cell Transplantation

A patient with a metastatic tumor and in need of an autologous bone marrow transplant is identified by a physician. As a first step in the treatment, the patient undergoes a bone marrow harvesting procedure. In this procedure, the patient is placed under general anesthesia in an operating room. The patients posterior iliac crest is then punctured multiple times by the surgeon and the bone marrow is aspirated.

The harvesting procedure results in retrieval of approximately $1 \times 10^9$ hematopoietic cells. The harvested cells are enriched for hematopoietic cells by being first run over an immunoaffinity column that selects for cells having the CD34 hematopoietic cell-specific surface antigen. To enrich the harvested cell population even further for stem cells, a second selection is performed by running the harvested cells over an immunoaffinity column that is bound with the anti-stem cell antibody, Thy-1.

After conventional elution from the column, the enriched hematopoietic cell population is thereafter contacted with CD34 antibodies that have been conjugated to a fluorochrome. The labeled antibodies specifically bind to the hematopoietic cells, but not the tumor cells. The cell population is then placed on a nominally flat surface at confluence. The cell density is a monolayer of approximately 500,000 cells per square centimeter An ultraviolet light that illuminates the fluorochrome-conjugated CD34 antibody is turned on to identify the hematopoietic cells.

An operator then targets a laser light from a Nitrogen laser. A laser beam with a wavelength of 375 nanometers and pulse length of five nanoseconds is used to manually target and kill each tumor cell that is identified because it did not fluoresce.

Once the non-fluorescent tumor cells have been destroyed, the remaining population is cryopreserved. Before the cells are re-introduced, the patient is given chemotherapeutic treatment to destroy the tumor cells that have metastasized throughout the patient's body. Following this treatment, the isolated cells are prepared for reintroduction by rapid thawing at 37° C. The tumor cell-free hematopoietic stem cells are then transplanted into the patient. The patient subsequently recovers with no remission of the original cancer.

Although the bone marrow harvesting and re-introduction procedures are usually carried out by a physician, the operator for the method of the present invention needs no medical training.

EXAMPLE 2

An experiment was performed to determine if Propidium Iodide (PI) could be used to confirm that a target cell, in a population of cells, was killed by laser treatment. As is known in the art, Propidium iodide is specific to double-stranded nucleic acids. Since PI can diffuse into the nucleus of dead cell, but can not penetrate the membrane of viable cell, we tested whether viability of target cells could be confirmed by PI color development in their nuclei.

Additionally, PI has an absorbance peak at 493 nm, which is close to the absorbance peak of the label phycoerythrin (PE) at 480 nm. Thus, the PI and PE could be activated by the same wavelength of light. In addition, PI has an emission peak of 617 nm, which was far enough to distinguish it from that of PE at 578 nm. Thus, a positive PE reading could be distinguished even when PE-labeled antibodies were bound to the cell.

Cell Line

The human hematopoietic cell line KG1a was obtained from the American Type Culture Collection (Rockville, Md.). Cells were received cryopreserved and then rapidly thawed and suspended in IMDM (Life Technologies, Grand Island, N.Y.) containing 4 mM L-glutamine, 3.024 g/L sodium bicarbonate and 20% fetal bovine serum. The cell line was passed every 3 to 4 days and maintained in an incubator at 37° C., 95% humidity and 5% $CO_2$ (as recommended by ATCC guidelines).

Cell Staining

The KG1a cells were stained by direct immunofluorescence staining of cell surface antigens using phycoerythrin (PE)-conjugated monoclonal antibodies against the human CD34 membrane antigen, as recommended in the manufacturer's guidelines (Becton Dickinson Immunocytometry Systems, San Jose, Calif.). The labeled KG1a cells (targets) were mixed with unstained KG1a cells (control population) in a ratio of 1:100.

Propidium iodide (Sigma Chemical Company, St. Louis, Mo.) was added to make a final concentration of 5 µg/mL in a cell suspension of $1.0 \times 10^6$ cells/mL. Each 20 µL aliquot of a mixed cell suspension of $1.0 \times 10^6$ cells/mL was added into wells of 384 well plate (Nalge Nunc International, Naperville, Ill.), and after 30 minutes for cell settling, image capture and laser ablation were carried out.

Cell Image Acquisition

Figure 2:
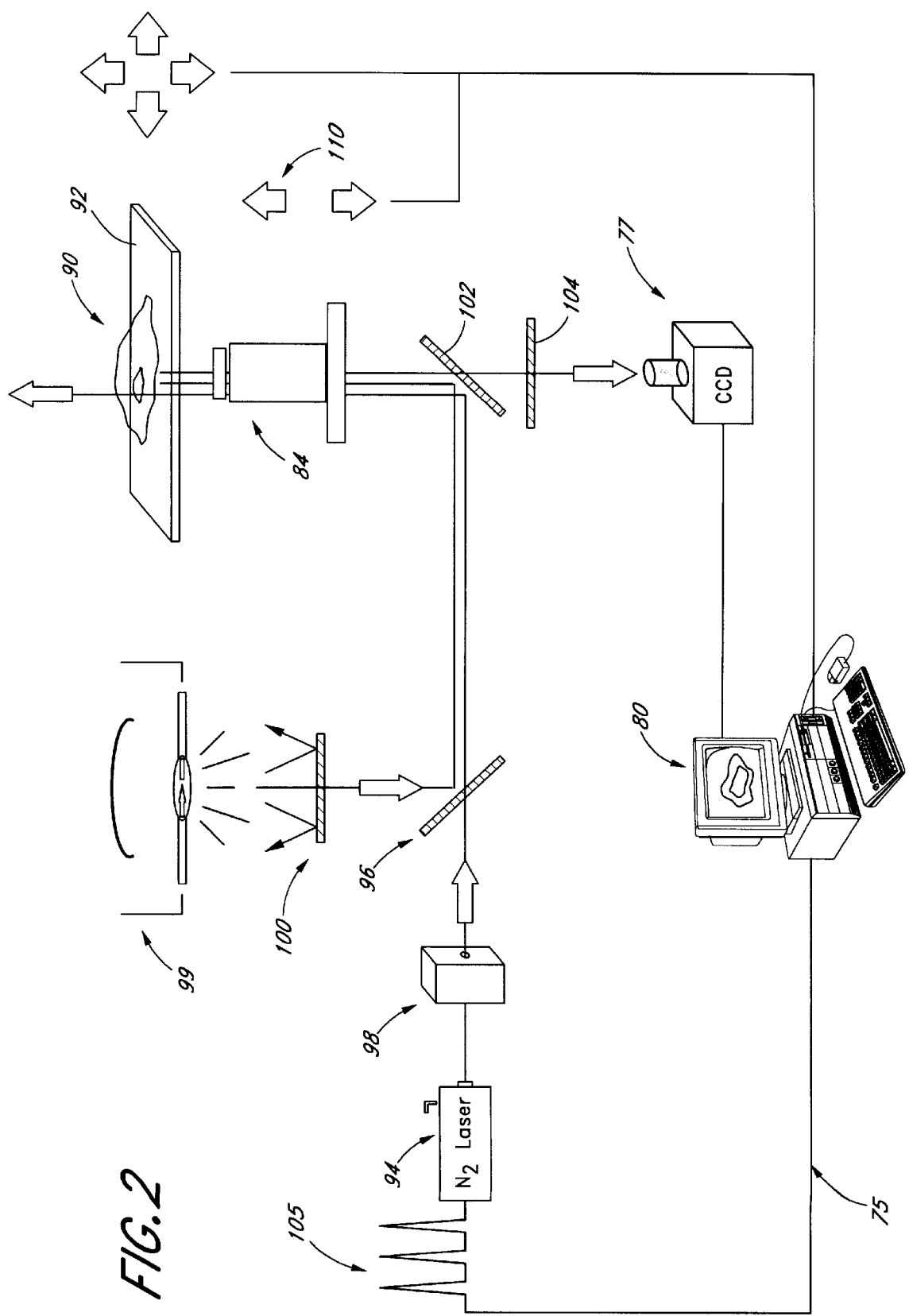
FIG. 2 is a diagram of another embodiment of an automated system for specifically targeting and killing labeled cells.

FIG. 2 illustrates a schematic diagram of one embodiment of a laser ablation system 75. The system includes a Charged Couple Device (CCD) camera 77 linked to a personal computer 80. The personal computer 80 was a SGI $O_2$ workstation (Silicon Graphics, Mountain View, Calif.). Digitized cell images were captured by the cooled CCD camera 77 (Photometrics Inc., Tucson, Ariz.) that had been installed in an inverted Diaphot 300 fluorescent microscope (Nikon Inc., Melville, N.Y.) with a 20× objective 84.

A selective fluorescent filter 86 (Set B2A; Chroma Technology Corp., Brattleboro, Vt.) was used to acquire a bright PE emission image. The captured images were displayed and processed by Isee™ software (Inovision Corp., Durham, N.C.) running on the personal computer 80.

The software provided complete automation for the system including stage tool operation, z-direction focus, coordination of regions of interest (e.g. targets) and laser control. There were 63 viewing image fields in each well of the 384 well plate and stepwise movement between fields was correctly controlled by the stage tool software routine within Isee. Each target cell 90 in the viewing field was identified under given parameters such as brightness, size and shape, and their locations were coordinated and marked by a feature extracting function in the Isee™ software. During the procedure, the target cells remained stationary on the surface 92 of their flasks.

Laser Ablation

A certified class IIIb nitrogen laser 94, model VSL-337 (The Laser Science Inc., Newton, Mass.) equipped with a beam splitter 96 and a Coumarin 440 dye cell 98 unit (Photonic Instruments, Arlington Heights, Ill.) was used to kill individual cells. The beam splitter 96 passed light from the laser 94, but refracted the blue light emitted from a Mercury arc lamp 99. Thus, light from the mercury arc lamp 99 and laser 94 were sent along the same pathway towards the target cell 90.

The mercury arc lamp transmitted light having a wavelength range between 450 nm and 490 nm. However, as indicated in FIG. 2, the blue light from the mercury arc lamp 99 was passed through a D470/40 excitation filter 100 (Chroma Technology Corp., Brattleboro, Vt.) in order to activate the PE conjugates attached to the CD34 surface antigen of the KG1a cells. Accordingly, the same pathway carried the excitation light and laser light.

The combination of laser light and excited mercury arc lamp light was then passed into a second beam splitter 102.

The beam splitter 102 refracted the light from the laser 94 and mercury arc lamp 99 through the microscope objective 84 to the target cell 90. The beam splitter 102 also transmits the light that is illuminated by the labeled target cell through a filter 104 and into the CCD camera 77.

It should be noted that during a normal procedure, the laser light is only transmitted for brief instances. In contrast, the mercury arc lamp light is normally transmitted constantly so that each of the labeled cells will reflect light through the beam splitter 102, filter 104 and into the CCD camera 77.

A pulse generator 105 links the laser 94 to provide the shortest burst of laser light necessary to kill the target cell 90, Shorter pulse lengths are more desirable because there is less chance that surrounding cells will be damaged through local heating of the cellular media.

Digital images of a field of stained target cells were captured and their locations were coordinated and marked by the Isee software system. Because a the arc lamp 99 produces a broad-band light that fluoresces every labeled cell in on the dish, the computer system was able to gather and process an entire field of view at one time.

As cells were being fired upon by short pulses of light from the laser, a vertically movable z-motor 110 provided a mechanism for specifically focusing the laser light onto differing focal plans in the dish. The z-motor 110 is an electronically controlled motor attached to the objective 84. The z-motor is connected so that the objective 84 can be moved up and down in the vertical direction in order to fine focus the laser into various focal planes. In addition, the z-motor can be controlled by the computer system 80 in order to focus the laser light pulse from the bottom of the target cell 90 to the top of the target cell. Focussing the laser pulse with the z-motor compensated for cell position variations in the vertical direction caused by imperfectly flat tissue culture plate surfaces.

Determination of Successful Cell Destruction

After each cell was pulsed with the laser, the computer analyzed the spectrum at the PI emission peak of 617 nm. If the cell was killed by the laser, a peak emission at 617 nm would be found at the cell's original location. If a PI emission peak was not found, the laser would send another pulse of light energy to the cell's location. In this manner, each tumor cell in the population was confirmed to have been killed.

Conclusion

This invention enables physicians to effectively treat patients in need of hematopoietic cell transplants without the risk of relapse due to re-introduction of cancerous cells. The targeted method described herein provides a method for the complete or almost complete removal of contaminating tumor cells from a hematopoietic stem cell or other cell population.

The invention may be embodied in other specific forms without departing from its spirit or essential characteristics. The described embodiments are to be considered in all respects only as illustrative and not restrictive. The scope of the invention is, therefore, indicated by the appended claims rather than by the foregoing descriptions. All charges which come within the meaning and range of equivalency of the claims are to be embraced within their scope.

I claim:

1. A method for eliminating a first population of cells from a second population of cells, comprising:
   a) labeling said first population of cells so that said first population of cells can be distinguished from said second population of cells;
   b) placing said first population of cells and said second population of cells is in a stationary position on a surface;
   c) locating one cell in said first population of cells by reference to said label;
   d) applying a first pulse from a controlled energy source to said one cell;
   e) determining if said one cell was killed by said first pulse; and
   f) applying a second pulse from a controlled energy source if said one cell was not killed.

2. The method of claim 1, wherein the method of labeling said first population of cells comprises labeling tumor cells.

3. The method of claim 1, wherein the method of eliminating a first population of cells from a second population of cells comprises eliminating a first population of tumor cells from a second population of non-tumor cells.

4. The method of claim 1, wherein the method of applying a first pulse comprises applying a laser pulse.

5. The method of claim 1, wherein the method of applying a second pulse comprises applying a laser pulse.

6. A method of eliminating tumor cells from within a cell population that includes non-tumor cells, comprising the steps of:
   a) labeling said non-tumor cells so that the non-tumor cells can be distinguished from said tumor cells;
   b) locating one of said tumor cells by identifying a non-labeled cell in said cell population; and
   c) killing said tumor cell by applying a pulse from a controlled energy source to said located tumor cell while said tumor cell is in a substantially stationary position on a surface.

7. The method of claim 6, wherein the step of killing said tumor cell comprises applying a laser pulse.

8. The method of claim 6, wherein the step of killing said tumor cell comprises applying a controlled energy source to said located tumor cell while said tumor cell is in a stationary position on a nominally flat surface.

9. The method of claim 6, wherein the step of killing said tumor cell comprises applying a controlled energy source to a located tumor cell while said cell population is at confluence.

10. A method of killing a first population of cells within a mixture of cells, said mixture comprising said first population of cells and a second population of cells, comprising:
    a) illuminating a portion of said mixture of cells, wherein said first population of cells or said second population of cells is labeled such that they are substantially distinguishable from one another;
    b) capturing an image of a plurality of cells in the illuminated portion of said mixture of cells;
    c) determining at least two dimensional coordinates of a cell of said first population of cells by reference to the captured image, and by reference to the presence of, or lack of, the label on said cell; and
    d) applying a lethal dose of energy to the coordinates of said cell.

11. The method of claim 10, wherein said label is specific for said first population of cells.

12. The method of claim 10, wherein said label is specific for said second population of cells.

13. The method of claim 10, wherein said image is captured with a camera.

14. The method of claim 10, wherein said first population of cells is comprised of tumor cells, and said second population of cells is comprised of non-tumor cells.

15. The method of claim 10, wherein said lethal dose of energy is from a laser source.

16. The method of claim 15, wherein the wavelength of energy emitted from said laser source is approximately between 100 nanometers to 30 micrometers.

17. The method of claim 10, additionally comprising:
   a) determining whether said cell was killed by said lethal dose of energy; and
   b) applying a second lethal dose of energy to said cell if said cell was not killed.

18. The method of claim 10, wherein said mixture of cells is in a substantially stationary position.

19. The method of claim 10, wherein said mixture of cells is on a substantially flat surface.

20. The method of claim 10, wherein said mixture of cells is substantially confluent on a surface.

21. The method of claim 10, wherein said mixture of cells is present as a substantially single layer of cells on a surface.

22. The method of claim 10, wherein (c) and (d) are repeated for every cell in said first population of cells that is captured in said image.

23. The method of claim 10, wherein said first population of cells is comprised of tumor cells, and said second population of cells is comprised of hematopoietic cells.

24. The method of claim 23, wherein said hematopoietic cells are comprised of cells that have been enriched for hematopoietic stem cells.

25. The method of claim 24, wherein said hematopoietic stem cells are enriched based on expression of the CD34 surface protein.

26. The method of claim 24, wherein said hematopoietic stem cells are enriched based on the expression, or lack of expression, of one or more cell markers.

27. The method of claim 26, wherein said hematopoietic stem cells are enriched based on expression, or lack of expression, of a cell marker selected from the group consisting of: Thy-1, CD38, CD15, CD11b, Gly-A, CD3, and CD19.

28. The method of claim 24, wherein said hematopoietic stem cells are enriched by using deep bed filtration or counterflow elutriation.

29. The method of claim 10, wherein said method of killing is at least partially performed under the control of a computer.

30. The method of claim 10, wherein said first population of cells is comprised of fibroblast cells, and said second population of cells is comprised of cartilage cells.

31. The method of claim 10, wherein said first population of cells is comprised of T cells.

32. The method of claim 10, wherein said first population of cells is comprised of non-tumor cells, and said second population of cells is comprised of tumor cells.

* * * * *